United States Patent [19]
Herrmann et al.

[11] Patent Number: 5,616,734
[45] Date of Patent: Apr. 1, 1997

[54] PROCESS FOR THE CATALYTIC OXIDATION OF AROMATIC COMPOUNDS

[75] Inventors: Wolfgang A. Herrmann, Freising; Joao D. G. Correia, München; Richard Fischer, Frankfurt; Waldemar Adam, Würzburg, all of Germany; Jianhua Lin, Singapore, Singapore; Chantu R. Saha-Möller, Würzburg, Germany; Masao Shimizu, Ibaraki, Japan

[73] Assignee: Hoechst Aktiengesellschaft, Frankfurt, Germany

[21] Appl. No.: 378,231

[22] Filed: Jan. 25, 1995

[30] Foreign Application Priority Data

Jan. 27, 1994 [DE] Germany .......................... 44 02 333.2
Jun. 6, 1994 [DE] Germany .......................... 44 19 799.3

[51] Int. Cl.[6] .......................... C07D 311/74; C07C 50/10; C07C 50/04
[52] U.S. Cl. .......................... 549/406; 552/292; 552/293; 552/296; 552/307; 552/309; 552/269; 562/408; 568/342; 568/803
[58] Field of Search .......................... 552/292, 296, 552/269, 309, 293, 307; 568/803, 342; 549/406; 562/408

[56] References Cited

U.S. PATENT DOCUMENTS 5,155,247 10/1992 Hermann et al. .

FOREIGN PATENT DOCUMENTS 0380085 8/1990 European Pat. Off. .
0560488 9/1993 European Pat. Off. .

*Primary Examiner*—Kimberly J. Prior
*Attorney, Agent, or Firm*—Curtis, Morris & Safford, P.C.

[57] ABSTRACT

The invention relates to the use of compounds of the formula I $$R^1_a Re_b O_c \qquad (I),$$

where a is from 1 to 6, b is from 1 to 4 and c is from 1 to 14 and the sum of a, b and c is in accordance with the valence of from 5 to 7 of the rhenium, with the proviso that c is not greater than 3·b, and where $R^1$ is identical or different and is an aliphatic hydrocarbon radical having from 1 to 10 carbon atoms, an aromatic hydrocarbon radical having from 6 to 10 carbon atoms or an arylalkyl radical having from 7 to 9 carbon atoms, with the radicals $R^1$ being able, if desired, to be identically or differently substituted independently of one another and, in the case of σ-bonded radicals, at least one hydrogen atom still being bonded to the carbon atom in the α position, as catalysts for the oxidation of electron-rich aromatic compounds and their derivatives and to a process for the oxidation of electron-rich aromatic compounds which comprises oxidizing electron-rich $C_6$–$C_{22}$-aryl compounds and their derivatives in the presence of a catalyst of the formula I and a peroxide-containing compound.

15 Claims, No Drawings

PROCESS FOR THE CATALYTIC OXIDATION OF AROMATIC COMPOUNDS

For the oxidation of unsaturated organic compounds (olefins, polyenes, alkynes, etc.), a very wide variety of, mostly binary oxides of transition metals have become established in practice as catalysts. Examples which may be mentioned are $V_2O_5$, $CrO_3$, $MoO_3$, $WO_3$, $[MnO_4]^-$, $OsO_4$ and $RuO_4$ as efficient epoxydation, hydroxylation or carboxylation catalysts (H. A. Jørgensen, Chem. Rev. 1989, pp. 431–458).

The use of such systems for the catalytic oxidation of aromatic compounds is, however, subject to many limitations. Lack of activity ($WO_3$) on the one hand and unsatisfactory selectivity on the other hand ($CrO_3/H_2SO_4$), besides acceptability from an ecological and health or pharmacological point of view, which is often not ensured (e.g. in the case of $CrO_3$ or $OsO_4$), have hitherto prevented the industrial use of such catalysts.

Other processes established in oxidation chemistry which use, for example, electrochemical oxidation, cerium(IV) salts, manganese(III) sulfate or peracids or peroxides (t-BuOOH) in the presence of molybdenum complexes as oxidants have, in the oxidation of simple or condensed aromatics or their derivatives, proven to be very complicated, expensive, often encumbered by high salt loadings resulting from the required stoichiometric use (cerium(IV) salts, manganese(III) sulfate) and usually also nonspecific (R. P. Kreh et al., J. Org. Chem., 1989, 54, 1526–1531; M. Hudlicky, Oxidations in Organic Chemistry, ACS Monograph 186, Washington/D.C., 1990, pp. 92–98; T. A. Gorodetskaya et al., U.S.S.R. Patent 1 121 255, 1984; Chem. Abstr., 1985, 102, 203754; W. Adam et al., Synthesis, 1993, 280–282, J. Skarzewski, Tetrahedron, 1984, 40, 4997–5000; S. Yamaguchi et al., Bull. Chem. Soc. Jpn., 1986, 59, 2881–2884; M. Periasamy, M. V. Bhatt, Tetrahedron Lett. 1978, 4561–4562; Y. Asakawa et al., 1988, J. Org. Chem., 53, 5453–5457; W. Chen, Chem. Abstr., 1987, 107, 58620). Studies by Buchler et al. (DE-A-3731689, DE-A-3731690) have shown that rhenium complexes epoxidize olefins, but not aromatics.

EP-A-380085 discloses organorhenium compounds which are used as catalysts for the oxidation of olefins in the presence of hydrogen peroxide. Since experience has shown that classical olefin oxidation catalysts are unsuitable for the oxidation of aromatic compounds, it could not be expected that these organorhenium compounds could also be efficiently used for the oxidation of aromatics.

Quinones and, in particular, naphthoquinone derivatives are industrially valuable products both for further processing (9,10-anthraquinone is a base material for marine paints) and for direct use, for example as vitamins. Thus, 2-methyl-1, 4-naphthoquinone as vitamin $K_3$ is the basis of the vitamin K group. The basic skeleton of 2-methyl-1,4-naphthoquinone is common to all fat-soluble K vitamins; differences occur only in the side chains of the 3 position. Just the direct synthesis of vitamin $K_3$ from the precursor 2-methylnaphthalene means an increase in value by a factor of about ten. Lack of vitamin K leads to a lowering of the level of clotting factors in the blood and thus to corresponding problems in blood clotting, which can be restored by doses of vitamin K.

It is therefore an object of the invention to find an effective catalyst system which achieves the desired selectivity in the oxidation of aromatics and is as easy as possible to obtain, simple to handle and able to be stored.

It has now surprisingly been found that certain organorhenium compounds are suitable as highly active catalysts for the oxidation of aromatic compounds, in particular for the selective conversion into quinones, if they are used together with peroxide-containing compounds in a liquid medium.

The invention provides for the use of compounds of the formula I $$R^1_a Re_b O_c \qquad (I),$$

where a is from 1 to 6, b is from 1 to 4 and c is from 1 to 14 and the sum of a, b and c is in accordance with the valence of from 5 to 7 of the rhenium, with the proviso that c is not greater than 3·b, and where $R^1$ is identical or different and is an aliphatic hydrocarbon radical having from 1 to 10 carbon atoms, an aromatic hydrocarbon radical having from 6 to 10 carbon atoms or an arylalkyl radical having from 7 to 9 carbon atoms, with the radicals $R^1$ being able, if desired, to be identically or differently substituted independently of one another and, in the case of σ-bonded radicals, at least one hydrogen atom still being bonded to the carbon atom in the α position, as catalysts for the oxidation of electron-rich aromatic compounds and their derivatives.

The compounds of the formula I can also be in the form of their Lewis base adducts.

For the purposes of the present invention, aliphatic hydrocarbon radicals are alkyl radicals having from 1 to 10 carbon atoms, alkenyl or alkynyl radicals having from 2 to 10 carbon atoms, cycloalkyl or cycloalkenyl having from 3 to 10 carbon atoms.

Suitable radicals are alkyl radicals $R^1$ such as methyl, ethyl, propyl, isopropyl and the various butyl radicals, pentyl radicals, hexyl radicals, octyl radicals such as ethylhexyl radicals and decyl radicals, and also alkenyl radicals such as allyl; also suitable are cycloalkyl radicals such as cyclopropyl, cyclobutyl, cyclopentyl, cyclohexyl, alkylated cyclohexyl such as hydrogenated tolyl, xylyl, ethylphenyl, cumyl or cymyl, 1-menthyl and 1-norbornyl and also alkenyl radicals such as vinyl and allyl and cycloalkenyl radicals such as cyclopentadienyl and pentamethylcyclopentadienyl. Methyl is particularly preferred.

Suitable aryl radicals $R^1$ are, for example, phenyl or naphthyl. As an example of an arylalkyl radical, mention may be made of benzyl.

While the alkyl, cycloalkyl and arylalkyl radicals $R^1$ are always σ-bonded to the Re central atom, the alkenyl, alkynyl, cycloalkenyl and aryl radicals $R^1$ can be σ- or π-bonded to the Re central atom.

The radical $R^1$ can be substituted, for example, by fluorine, chlorine, bromine, $NH_2$, $NHR^2$, $NR^2_2$, $PH_3$, $PHR^2_2$, $PH_2R^2$, $PR^2_3$, OH or $OR^2$, where $R^2$ is identical or different and is an alkyl radical having from 1 to 10 carbon atoms or an aryl radical having from 6 to 10 carbon atoms.

A typical example of a Lewis base adduct of compounds of the formula I is $CH_3ReO_3$·bipyridine.

For steric reasons it is favorable if the compound of the formula I bears not more than three groups having more than 6 carbon atoms per rhenium atom; the compounds advantageously contain only one such group.

Preference is given to $C_3$–$C_3$-alkyltrioxorhenium complexes, in particular methyltrioxorhenium.

The invention further provides a process for the oxidation of electron-rich aromatic compounds, which comprises oxidizing electron-rich $C_6$–$C_{22}$-aryl compounds and their derivatives in the presence of a catalyst of the formula I $$R^1_a Re_b O_c \qquad (I),$$

where $R^1$, a, b and c are as defined above, and a peroxide-containing compound in a liquid medium.

Suitable aryl compounds for the process of the invention are electron-rich aromatic compounds or condensed aromatic systems having from 6 to 22 carbon atoms, preferably having from 6 to 14 carbon atoms, which can be unsubstituted or monosubstituted or polysubstituted, identically or differently, by an electron donor group. Typical suitable electron donor groups are hydroxyl, $C_1$–$C_3$-alkoxy, N-acylamino, N-acylamino-$C_1$–$C_3$-alkyl, acyloxy and $C_1$–$C_3$-alkyl.

Examples of such aryl compounds are xylenes, disubstituted, trisubstituted or tetrasubstituted $C_1$–$C_3$-alkylbenzenes or $C_1$–$C_3$-alkoxybenzenes, naphthalene and its monosubstituted to hexasubstituted $C_1$–$C_3$-alkyl or $C_1$–$C_3$-alkoxy derivatives, anthracene and its $C_1$–$C_3$-alkyl or $C_1$–$C_3$-alkoxy derivatives, phenanthrene and higher condensed aromatics, phenol, hydroquinone, resorcinol, catechol and pyrogallol, but also biphenyl.

Preferred aryl compounds are naphthalene and anthracene and their derivatives; particular preference is given to naphthalene and its derivatives, in particular 2-methylnaphthalene.

By means of the process of the invention, the aryl compounds are generally oxidized to the corresponding quinoid systems. For example, 2-methylnaphthalene gives 2-methyl-1,4-naphthoquinone, the basis of the vitamin K series.

In the case of higher-substituted (triply and more) aryl compounds in which the formation of a quinoid system is not possible, the process of the invention gives the corresponding hydroxyl compound.

Typical examples of such higher-substituted aryl compounds are 1,2,3,5,8-pentamethylnaphthalene; 1,2,3-trimethylbenzene, mesitylene and 1,3,5-trimethoxybenzene. In the process of the invention, these starting materials give, for example, the following hydroxyl compounds: 4-hydroxy-1,2,3,5,8-pentamethylnaphthalene, 1-hydroxy-3,4,5-trimethylbenzene, 1-hydroxy-2,4,6-trimethylbenzene and 1-hydroxy-2,4,6-trimethoxybenzene.

According to the process of the invention, the aromatic compound to be oxidized is dissolved in an organic solvent and admixed with the catalyst.

The concentration of the dissolved aromatic compound is 0.1 mol in 10–1,000 ml, preferably 0.1 mol in 25–250 ml, particularly preferably 0.1 mol in 50–200 ml, of solvent. Suitable organic solvents are, for example, glacial acetic acid, THF, tert-butanol or tert-butyl methyl ether, preferably glacial acetic acid or THF. The catalyst can be used in an amount of 0.01–10.0 mol %, preferably 0.1–2.0 mol %. The peroxide-containing compound (5–90% by weight) is added to this solution in a molar ratio of from 1:1 to 20:1, based on the aromatic compounds to be oxidized.

The reaction mixture is stirred until completely reacted at a temperature of 10°–100° C., preferably 20°–60° C.

The reaction mixture is then worked up in a manner customary to those skilled in the art, i.e., for example, neutralized, extracted and dried. The crude oxidation product can, for example, be further purified by high-vacuum distillation or by recrystallization.

The organorhenium compounds of the formula I are known (W. A. Herrmann el al., Angew. Chem. 100 (1988), 420–422; EP-A-380085), but their suitability as oxidation catalyst for aromatics is new and could not have been expected under any circumstances. Rather, these are the first rhenium compounds of any type which can be successively used for the oxidation of aromatics. Owing to their solubility properties, they are particularly suitable as homogeneous catalysts. Their particular advantage is also that they can be synthesized in a simple manner from commercial $Re_2O_7$ by means of customary substances acting as transferrers of organic groups, e.g. in the case of $R^1$=$CH_3$ by reaction with commercial tetramethyltin or commercial dimethylzinc. They are insensitive to air and moisture, water and acid, can be stored at room temperature, and in combination with peroxide-containing compounds such as hydrogen peroxide, inorganic peroxides such as alkali metal peroxides, in particular sodium peroxide, and also percarboxylic acids and their salts such as m-chloroperbenzoic acid, peracetic acid and magnesium monoperoxophthalate are highly active catalysts for the oxidations of the invention. Preference is given to using the compounds of the formula I in combination with hydrogen peroxide.

EXAMPLES

General Procedure for the Rhenium-Catalyzed Oxidation of Aromatic Compounds

The substrates to be oxidized were dissolved in glacial acetic acid or THF and admixed with the catalyst. Finally, hydrogen peroxide was added as oxidant. The reaction mixture was stirred until completely reacted at 20°, 40° or 60° C. (see table).

Work-up:

The reaction solution was neutralized with a saturated sodium hydrogen carbonate solution. The aqueous mother liquor was extracted three times with methylene chloride, and the combined extracts were dried over $MgSO_4$. The solvent was then removed in vacuo. After removal of the methylene chloride, yellow colored, solid oxidation products were generally obtained. The examples carried out in accordance with the above procedure are shown in Table 1. Example No. 2 is a comparative example.

TABLE 1

Oxidation examples in accordance with the general procedure with associated reaction conditions

| No. | Aryl compound (5 mmol in each case) | Catalyst | T (°C.) | t (h) | Conversion (%) | Product (%) | |
|---|---|---|---|---|---|---|---|
| 1 | 2-methyl-naphthalene | 0.10 mmol MTO | 20 | 4 | 75 | 2-methyl-1,4-naphthoquinone 86 | 2-methyl-5,8-naphthoquinone 14 |
| 2 | 2-methyl-naphthalene | — | 20 | 4 | 0 | 0 | 0 |

TABLE 1-continued

Oxidation examples in accordance with the general procedure with associated reaction conditions

| No. | Aryl compound (5 mmol in each case) | Catalyst | T (°C.) | t (h) | Conversion (%) | Product (%) | |
|---|---|---|---|---|---|---|---|
| 3 | 2-methyl-naphthalene | 0.10 mmol MTO | 20 | 24 | 85 | 2-methyl-1,4-naphthoquinone 86 | 2-methyl-5,8-naphthoquinone 14 |
| 4 | 2-methyl-naphthalene | 1.10 mmol MTO in THF | 20 | 48 | 86 | 2-methyl-1,4-naphthoquinone 86 | 2-methyl-5,8-naphthoquinone 14 |
| 5 | 2,3-dimethyl-naphthalene | 0.10 mmol MTO | 20 | 4 | 73 | 2,3-dimethyl-1,4-naphthoquinone 98 | 2,3-dimethyl-5,8-naphthoquinone 2 |
| 6 | 2,3,5,9-tetramethyl-naphthalene | 0.10 mmol MTO | 20 | 4 | 100 | 2,3,5,8-tetramethyl-naphthoquinone 100 | — |
| 7 | phenanthrene | 0.1 mmol MTO | 60 | 4 | 80 | biphenyl-1,10-dicarboxylic acid | |
| 8 | resorcinol | 0.1 mmol MTO | 20 | 4 | 63 | 2-hydroxyquinone 50 | |
| 9 | phenol | 0.10 mmol MTO | 40 | 4 | 80 | quinone 65 | |
| 10 | 1,2-dimethyl-naphthalene | 0.2 mmol MTO | 20 | 4 | 67 | 1,2-dimethyl-5,8-naphthoquinone 21 | 1,2-dimethyl-5,8-dihydroxy-naphthalene 46 |
| 11 | mesitylene | 0.1 mmol MTO in 22 ml AcOH | 20 | 4 | 69 | 4-hydroxy-mesitylene 65 | — |
| 12 | 2,3-dimethyl-naphthalene | 0.1 mmol allylReO$_3$ in 22 ml THF | 20 | 3 | 45 | 2,3-dimethyl-1,4-naphtho-quinone 40 | — |
| 13 | 2,3-dimethyl-naphthalene | 0.1 mmol CpReO$_3$ in 22 ml THF | 20 | 24 | 45 | 2,3-dimethyl-1,4-naphtho-quinone 45 | — |

Solvent: No. 1–10, 11 ml of acetic acid in each case (or THF, see table);

MTO=methyltrioxorhenium;

85% $H_2O_2$: molar ratio aryl compound/$H_2O_2$=1:20;

Cp=cyclopentadienyl.

We claim:

1. A process for the oxidation of electron-rich aromatic compounds, which comprises oxidizing an aromatic ring of electron-rich $C_6$–$C_{22}$-aryl compounds and their derivatives in the presence of a catalyst of the formula I

$$R^1{}_a Re_b O_c \qquad (I),$$

where a is from 1 to 6, b is from 1 to 4 and c is from 1 to 14 and the sum of a, b and c is in accordance with the valence of from 5 to 7 of the rhenium, with the proviso that c is not greater than 3·b, and where $R^1$ is identical or different and is an aliphatic hydrocarbon radical having from 1 to 10 carbon atoms, an aromatic hydrocarbon radical having from 6 to 10 carbon atoms or an arylalkyl radical having from 7 to 9 carbon atoms, with the radicals $R^1$ being able, if desired, to be identically or differently substituted independently of one another and, in the case of σ-bonded radicals, at least one hydrogen atom still being bonded to the carbon atom in the α position, and a peroxide-containing compound.

2. The process as claimed in claim 1, wherein the peroxide-containing compound used is hydrogen peroxide.

3. The process as claimed in claim 1, wherein a $C_6$–$C_{14}$-aryl compound is oxidized.

4. The process as claimed in claim 1, wherein naphthalene or one of its derivatives is oxidized.

5. The process as claimed in claim 1, wherein 2-methyl-naphthalene is oxidized.

6. The process as claimed in claim 1, wherein said aliphatic hydrocarbon radicals are alkyl radicals selected from the group consisting of methyl, ethyl, propyl, isopropyl, butyl, pentyl, hexyl, octyl and decyl.

7. The process as claimed in claim 6, wherein said alkyl radical is methyl.

8. The process as claimed in claim 1, wherein said aryl compounds are selected from the group consisting of xylenes, disubstituted, trisubstituted or tetrasubstituted $C_1$–$C_3$-alkylbenzenes or $C_1$–$C_3$-alkoxybenzenes, naphthalene and its monosubstituted to hexasubstituted $C_1$–$C_3$-alkyl or $C_1$–$C_3$-alkoxy derivatives, anthracene and its $C_1$–$C_3$-alkyl or $C_1$–$C_3$-alkoxy derivatives, phenanthrene and higher condensed aromatics, phenol, hydroquinone, resorcinol, catechol, pyrogallol and biphenyl.

9. The process as claimed in claim 1, wherein anthracene or one of its derivatives is oxidized.

10. The process as claimed in claim 1, wherein said aryl compounds are monosubstituted or polysubstituted, identically or differently, by an electron donor group selected from the group consisting of hydroxyl, $C_1$–$C_3$-alkoxy, N-acylamino, N-acylamino-$C_1$–$C_3$-alkyl, acyloxy and $C_1$–$C_3$-alkyl.

11. The process as claimed in claim 1, wherein said aromatic compound is dissolved in an organic solvent and admixed with said catalyst to form a reaction mixture which has a concentration of 0.1 mol dissolved aromatic compound in 25–250 milliliter solvent.

12. The process as claimed in claim 11, wherein said organic solvent is selected from the group consisting of glacial acetic acid, THF, tert-butanol and tert-butyl methyl ether.

13. The process as claimed in claim 11, wherein said catalyst is present in an amount ranging from 0.01 to 10 mol %.

14. The process as claimed in claim 11, wherein said catalyst is present in an amount ranging from 0.1 to 2 mol %.

15. The process as claimed in claim 11, wherein said reaction mixture is stirred at a temperature from 20°–60° C. until completely reacted.

* * * * *